(12) United States Patent
Meyerson et al.

(10) Patent No.: US 10,835,120 B2
(45) Date of Patent: Nov. 17, 2020

(54) EXTENDED MEDICAL TEST SYSTEM

(71) Applicant: Welch Allyn, Inc., Skaneateles Falls, NY (US)

(72) Inventors: Craig M. Meyerson, Syracuse, NY (US); David J. Maier, Skaneateles, NY (US); Tyson B. Whitaker, Arden, NC (US); Scott Andrew Martin, Warners, NY (US); Timothy R. Fitch, Syracuse, NY (US); Kirsten M. Emmons, Batesville, IN (US); Andrew David Clark, Waltham, MA (US); Aalok Mehta, Singapore (SG); Frederic Bregeon, Saint-Avé (FR); Stephen C. Daley, Skaneateles, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 285 days.

(21) Appl. No.: 15/244,489

(22) Filed: Aug. 23, 2016

(65) Prior Publication Data
US 2018/0055357 A1    Mar. 1, 2018

(51) Int. Cl.
| | |
|---|---|
| A61B 5/05 | (2006.01) |
| A61B 3/14 | (2006.01) |
| A61B 5/00 | (2006.01) |
| A61B 5/1171 | (2016.01) |
| A61B 5/103 | (2006.01) |
| A61B 3/18 | (2006.01) |

(52) U.S. Cl.
CPC .............. *A61B 3/14* (2013.01); *A61B 3/18* (2013.01); *A61B 5/0077* (2013.01); *A61B 5/1032* (2013.01); *A61B 5/1176* (2013.01); *A61B 5/7282* (2013.01); *A61B 5/743* (2013.01); *A61B 2560/0431* (2013.01); *A61B 2576/00* (2013.01)

(58) Field of Classification Search
CPC ............................ G06F 3/013; G02B 27/0093
See application file for complete search history.

(56) References Cited

U.S. PATENT DOCUMENTS

| | | | |
|---|---|---|---|
| 7,233,684 B2 * | 6/2007 | Fedorovskaya ... | G06F 17/30265 382/118 |
| 9,028,405 B2 * | 5/2015 | Tran .................. | A61B 5/0022 600/300 |
| 9,237,847 B2 | 1/2016 | Wang et al. | |
| 9,600,069 B2 * | 3/2017 | Publicover ......... | G06F 3/013 |

(Continued)

FOREIGN PATENT DOCUMENTS

| | | |
|---|---|---|
| DE | 3943097 A1 | 7/1991 |
| WO | 2014074157 A1 | 5/2014 |

OTHER PUBLICATIONS

VSP, "Diabetes Discovery—Via the Eyes", Retrieved on: Dec. 28, 2015, available at: https://www.vsp.com/diabetes.html.

(Continued)

*Primary Examiner* — Michael J D'Abreu
(74) *Attorney, Agent, or Firm* — Merchant & Gould P.C.

(57) ABSTRACT

An extended medical test system provides a user-friendly apparatus that can be used to perform a plurality of diagnostic functions. In an example of an eye examination system, the system is configured to capture one or more patient images containing a patient's eye and a surrounding body portion, and perform additional diagnostic functions as well as the eye examination.

18 Claims, 15 Drawing Sheets

(56) References Cited

U.S. PATENT DOCUMENTS

| | | | |
|---|---|---|---|
| 9,775,512 B1* | 10/2017 | Tyler | A61B 3/113 |
| 2004/0210159 A1* | 10/2004 | Kibar | A61B 5/4803 |
| | | | 600/558 |
| 2010/0280372 A1 | 11/2010 | Poolman et al. | |
| 2014/0098344 A1 | 4/2014 | Gierhart et al. | |
| 2014/0214047 A1 | 7/2014 | Sunalp et al. | |
| 2014/0275935 A1 | 9/2014 | Walsh et al. | |
| 2014/0348403 A1 | 11/2014 | Kurtz et al. | |
| 2014/0363058 A1 | 12/2014 | Emmett et al. | |
| 2016/0249804 A1 | 9/2016 | Wang | |

OTHER PUBLICATIONS

Eye-Controls, "Iris Technology Overview", Retrieved on: Dec. 28, 2015, available at: http://www.eye-controls.com/technology.

* cited by examiner

EXTENDED MEDICAL TEST SYSTEM

BACKGROUND

To identify a health problem, people typically see a primary care physician who provides the first contact for people with an undiagnosed health concern as well as continuing care of various medical conditions or diagnosis. Primary care physicians typically perform basic diagnosis and treatment of common illness and medical conditions, based on, for example, basic medical testing. More complex and time-intensive diagnostic procedures can be obtained by referral to specialists.

A vision or eye examination is one example of such healthcare practice. When people have concerns about their eyes, they can see primary care eye doctors, such as optometrists, who are trained to perform routine eye examination for both vision and health problems and correct refractive errors by prescribing eyeglasses and contact lenses. Some optometrists can also provide low vision care and vision therapy. When medical eye problems, such as glaucoma, macular degeneration or cataracts, are identified, primary care eye doctors can refer patients to specialists, such as ophthalmologists, for a definitive diagnosis and treatment of the particular eye problems. Ophthalmologists can diagnose and treat disease, prescribe medications, or preform eye surgery, as needed.

In case of eye examination, there are several eye exam instruments for evaluation of vision and eye health issues. Examples of such instruments include a keratometer (i.e., an ophthalomometer), an ophthalmoscope, and a tonometer. These eye examination tools are designed to perform dedicated diagnostic measurements and require different techniques for proper operation. Therefore, only healthcare practitioners who have knowledge and skills specific to the instruments can handle the instruments properly and perform diagnosis based on the readings from the instruments. Primary care practitioners who are not familiar with such instruments may find it difficult to diagnose a variety of health conditions on their own.

SUMMARY

In general terms, this disclosure is directed to an extended medical test system. In one possible configuration and by non-limiting example, the system includes a sensing device for obtaining one or more parameters associated with a patient, and an evaluation device for providing a diagnosis based on a change of such parameters. Various aspects are described in this disclosure, which include, but are not limited to, the following aspects.

One aspect is an apparatus for a medical test. The apparatus includes an image capture device configured to capture a patient image, the patient image including an eye and a surrounding facial portion around the eye, and an evaluation device configured to determine a point of interest in the patient image, determine a property associated with the point of interest from the patient image, compare the property with a reference property, and evaluate a change in the property.

Another aspect is a method of performing a medical test. The method includes obtaining a patient image, the patient image including an eye and a surrounding facial portion around the eye, determining a point of interest in the patient image, determining a property associated with the point of interest from the patient image, comparing the property with a reference property, and evaluating a change in the property.

DETAILED DESCRIPTION

Figure 1:
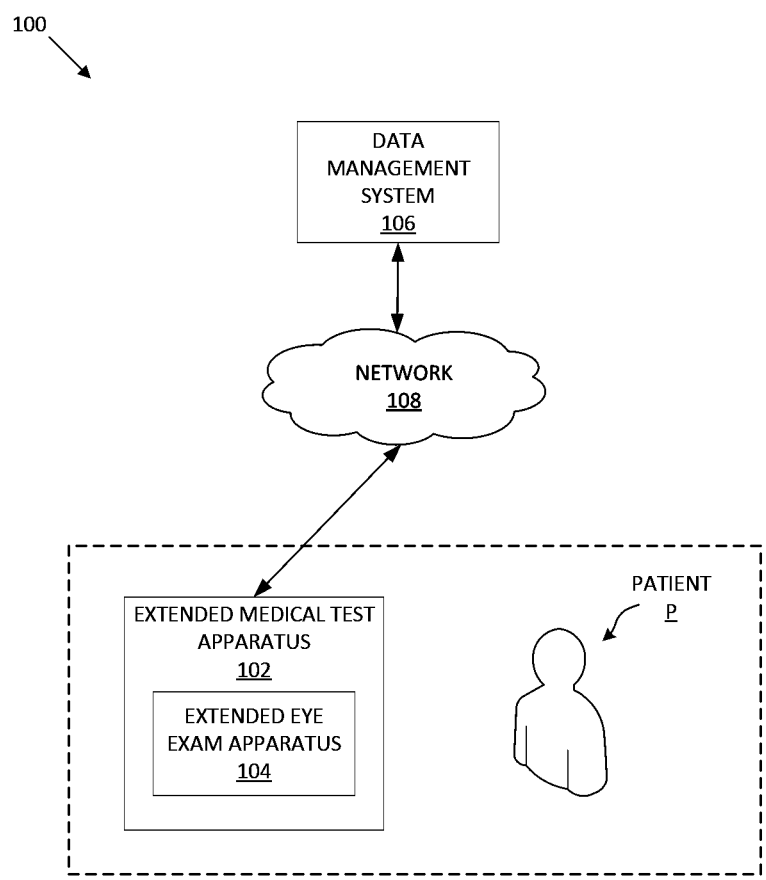
FIG. 1 is schematically illustrates an extended medical test system in accordance with an exemplary embodiment of the present disclosure.

Various embodiments will be described in detail with reference to the drawings, wherein like reference numerals represent like parts and assemblies throughout the several views.

In general, an extended medical test system in accordance with the present disclosure provides a user-friendly apparatus that can be used to perform a plurality of diagnostic functions. In eye examination cases, the system is configured to capture one or more patient images containing a patient's eye and a surrounding body portion (e.g., a facial portion), and perform additional diagnostic functions as well as the eye examination using the patient images. The system can obtain various types of readings at the same time as necessary, and therefore eliminate a need for a plurality of separate devices for testing different types of illnesses, diseases or other health conditions. The system can evaluate the readings obtained at different times and track a change over time, which can be used for diagnosing, and providing health-related recommendations for, a variety of illnesses and health status at the same time. As such, the system generates a set of reliable diagnostic data and other actionable information. The medical test system of the present disclosure is configured to be user-friendly so that anyone who does not have a specialized skillset in a relevant medical field can easily use the system. The system can be provided in various configurations, such as an attachment to a mobile computing device, an independent handheld device, a standalone station, and a walk-through frame.

FIG. 1 schematically illustrates an extended medical test system 100 in accordance with an exemplary embodiment of the present disclosure. The system 100 includes an extended medical test apparatus 102. The extended medical test apparatus 102 operates to detect an extensive medical test. The extended medical test apparatus 102 is configured to detect and monitor one or more parameters associated with a patient P to diagnose diseases, disease processes, and susceptibility and/or determine a course of treatment.

The extended medical test apparatus 102 can be of various types. In one embodiment, the extended medical test apparatus 102 includes or is configured as an extended eye examination apparatus 104. The extended eye examination apparatus 104 is configured to provide additional capabilities to typical eye examination. Such typical eye examination can be performed by a primary care practitioner or other practitioners who are not specialized in eye or vision care.

An eye examination may include a variety of tests and procedures. Such tests range from simple ones, such as having a patient read an eye chart, to complex tests, such as using a high-powered lens to visualize various structures inside the eye. A comprehensive eye examination is typically performed by optometrists, ophthalmologists, or other practitioners who have appropriate expertise in eye or vision care. Because of complexity of eye examination, a primary care physician or other practitioners who are less skilled than optometrists or ophthalmologists may have difficulty in performing extensive eye examination. A variety of sophisticating medical devices or instruments that are used for different eye examinations can allow healthcare practitioners examine patients for various illnesses or diseases.

The extended eye examination apparatus 104 is configured to be a user-friendly device that provides one or more additional diagnostic functionalities as well as a typical eye examination capability, so as to be conveniently used by a primary care physician, a patient, and other less skilled practitioners in eye examination. While being easily manipulable, the expended eye examination apparatus 104 provides reliable test results.

In some embodiments, the extended eye examination apparatus 104 operates to capture and evaluate not only the structures of the patent's eye but also at least a portion of the patient's face around the eye. Suitable image processing and evaluation enables monitoring the status of the eye and tracking the change in the eye structures as well as one or more physiological parameters, such as a body temperature, blood pressure, hydration, and a glucose level to name a few. An example of the extended eye examination apparatus 104 is further described with reference to FIG. 5.

With continued reference to FIG. 1, in some examples, the medical test apparatus 102 such as the eye exam apparatus 104 is operable to communicate with a data management system 106 via a data communication network 108. In some embodiments, the data management system 106 operates to process the data, such as digital image data, transmitted from the medical test apparatus 102 and evaluate the data to provide a diagnostic result, which is then transmitted to the medical test apparatus 102. In addition, the data management system 106 operates to manage the patient's personal and/or medical information, such as health conditions and other information. The data management system 106 stores and manages data associated with a plurality of patients together and can transmit any part or all of the data to a requesting system, such as the medical test apparatus 102. The data management system 106 can be operated by the healthcare practitioner and/or a healthcare service provider, such as a hospital or clinic. In some examples, the data management system 106 includes such a computing device as described in FIG. 3. Examples of the data management system 106 include Connex® data management systems available from Welch Allyn Inc., Skaneateles Falls, N.Y.

The data communication network 108 communicates digital data between one or more computing devices, such as among the medical test apparatus 102 such as the eye exam apparatus 104 and the data management system 106. Examples of the network 108 include a local area network and a wide area network, such as the Internet. In some embodiments, the network 108 includes a wireless communication system, a wired communication system, or a combination of wireless and wired communication systems. A wired communication system can transmit data using electrical or optical signals in various possible embodiments. Wireless communication systems typically transmit signals via electromagnetic waves, such as in the form of optical signals or radio frequency (RF) signals. A wireless communication system typically includes an optical or RF transmitter for transmitting optical or RF signals, and an optical or RF receiver for receiving optical or RF signals. Examples of wireless communication systems include Wi-Fi communication devices (such as utilizing wireless routers or wireless access points), cellular communication devices (such as utilizing one or more cellular base stations), and other wireless communication devices.

Figure 2:
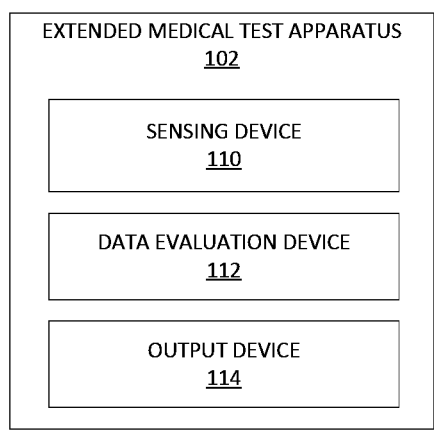
FIG. 2 is a block diagram illustrating an example of the extended medical test apparatus.

FIG. 2 is a block diagram illustrating an example of the extended medical test apparatus 102. The medical test apparatus 102 includes a physical structure configured to house and hold various components of the medical test apparatus 102. Such a physical structure can incorporate at least one of a sensing device 110, a data evaluation device 112, and an output device 114.

The sensing device 110 operates to capture one or more image of a patient and/or detect physiological parameters associated with the patient. An example of the sensing device 110 is described in FIG. 5.

The data evaluation device 112 operates to process the image and/or parameter data obtained by the sensing device 110 and evaluate them for diagnosis. In addition, the data evaluation device 112 can generate various pieces of healthcare information, such as advice or recommendation about the patient's condition. An example of the data evaluation device 112 is described in FIG. 8.

Figure 11:
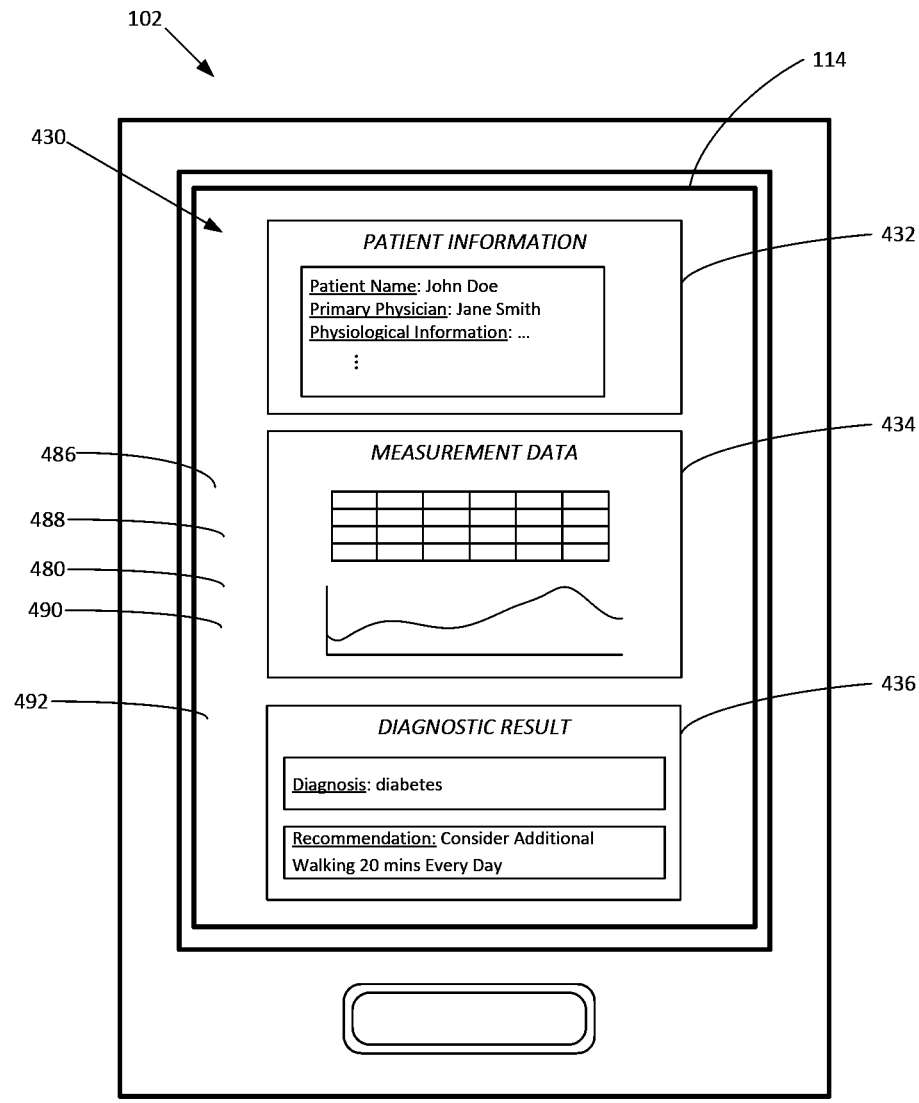
FIG. 11 schematically illustrates an example evaluation output presented by an output device of the medical test apparatus.

The output device 114 operates to present the information generated by the data evaluation device 112. In addition, the output device 114 can present the measurements or images obtained by the sensing device 110. An example output from the output device 114 is illustrated in FIG. 11.

Figure 3:
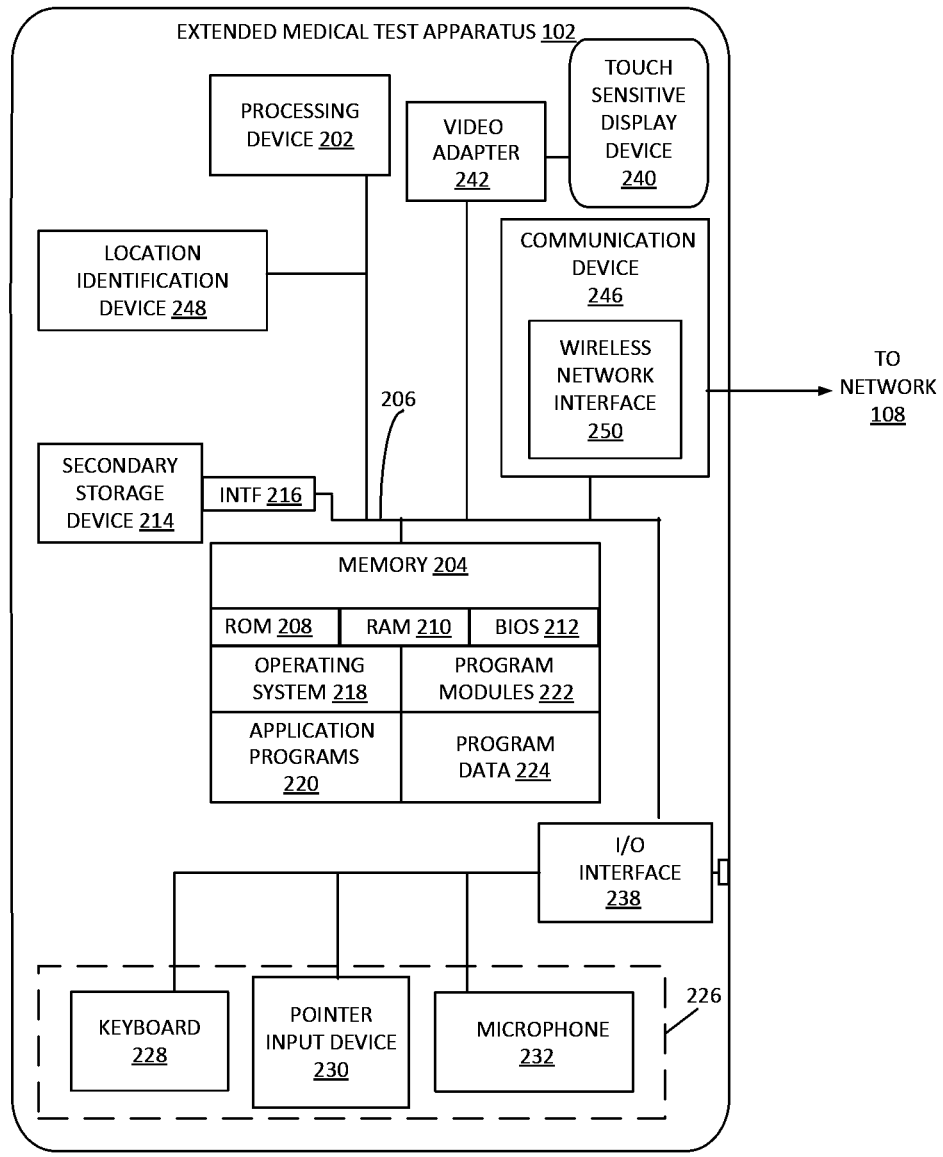
FIG. 3 illustrates an exemplary architecture of the extended medical test apparatus.

FIG. 3 illustrates an exemplary architecture of the extended medical test apparatus 102. The extended medical test apparatus 102 illustrated in FIG. 3 is used to execute the operating system, application programs, and software modules (including the software engines) described herein.

The extended medical test apparatus 102 is a computing device of various types. In some embodiments, the extended medical test apparatus 102 is a mobile computing device. Examples of the extended medical test apparatus 102 as a mobile computing device include a mobile device (e.g., a smart phone and a tablet computer), a wearable computer (e.g., a smartwatch and a head-mounted display), a personal digital assistant (PDA), a handheld game console, a portable media player, a ultra-mobile PC, a digital still camera, a digital video camera, and other mobile devices. In other embodiments, the extended medical test apparatus 102 is other computing devices, such as a desktop computer, a laptop computer, or other devices configured to process digital instructions.

It is recognized that the architecture illustrated in FIG. 3 can also be implemented in other computing devices used to achieve aspects of the present disclosure. For example, the data management system 106 can be configured similarly to the architecture of FIG. 3. To avoid undue repetition, this description of the extended medical test apparatus 102 will not be separately repeated herein for each of the other computing devices including the data management system 106.

The extended medical test apparatus 102 includes, in some embodiments, at least one processing device 202, such as a central processing unit (CPU). A variety of processing devices are available from a variety of manufacturers, for example, Intel or Advanced Micro Devices. In this example, the extended medical test apparatus 102 also includes a system memory 204, and a system bus 206 that couples various system components including the system memory 204 to the processing device 202. The system bus 206 is one of any number of types of bus structures including a memory bus, or memory controller; a peripheral bus; and a local bus using any of a variety of bus architectures.

The system memory 204 includes read only memory 208 and random access memory 210. A basic input/output system 212 containing the basic routines that act to transfer information within the extended medical test apparatus 102, such as during start up, is typically stored in the read only memory 208.

The extended medical test apparatus 102 also includes a secondary storage device 214 in some embodiments, such as a hard disk drive, for storing digital data. The secondary storage device 214 is connected to the system bus 206 by a secondary storage interface 216. The secondary storage devices and their associated computer readable media provide nonvolatile storage of computer readable instructions (including application programs and program modules), data structures, and other data for the extended medical test apparatus 102.

Although the exemplary environment described herein employs a hard disk drive as a secondary storage device, other types of computer readable storage media are used in other embodiments. Examples of these other types of computer readable storage media include magnetic cassettes, flash memory cards, digital video disks, Bernoulli cartridges, compact disc read only memories, digital versatile disk read only memories, random access memories, or read only memories. Some embodiments include non-transitory media.

A number of program modules can be stored in secondary storage device 214 or memory 204, including an operating system 218, one or more application programs 220, other program modules 222, and program data 224.

In some embodiments, the extended medical test apparatus 102 includes input devices to enable a user to provide inputs to the extended medical test apparatus 102. Examples of input devices 226 include a keyboard 228, a pointer input device 230, a microphone 232, and a touch sensitive display 240. Other embodiments include other input devices. The input devices are often connected to the processing device 202 through an input/output interface 238 that is coupled to the system bus 206. These input devices 226 can be connected by any number of input/output interfaces, such as a parallel port, serial port, game port, or a universal serial bus. Wireless communication between input devices and interface 238 is possible as well, and includes infrared, BLUETOOTH® wireless technology, 802.11a/b/g/n, cellular, or other radio frequency communication systems in some possible embodiments.

In this example embodiment, a touch sensitive display device 240 is also connected to the system bus 206 via an interface, such as a video adapter 242. The touch sensitive display device 240 includes touch sensors for receiving input from a user when the user touches the display. Such sensors can be capacitive sensors, pressure sensors, or other touch sensors. The sensors not only detect contact with the display, but also the location of the contact and movement of the contact over time. For example, a user can move a finger or stylus across the screen to provide written inputs. The written inputs are evaluated and, in some embodiments, converted into text inputs.

In addition to the display device 240, the extended medical test apparatus 102 can include various other peripheral devices (not shown), such as speakers or a printer.

The computing device 200 further includes a communication device 246 configured to establish communication across the network. In some embodiments, when used in a local area networking environment or a wide area networking environment (such as the Internet), the computing device 200 is typically connected to the network through a network interface, such as a wireless network interface 250. Other possible embodiments use other wired and/or wireless communication devices. For example, some embodiments of the computing device 200 include an Ethernet network interface, or a modem for communicating across the network. In yet other embodiments, the communication device 246 is capable of short-range wireless communication. Short-range wireless communication is one-way or two-way short-range to medium-range wireless communication. Short-range wireless communication can be established according to various technologies and protocols. Examples of short-range wireless communication include a radio frequency identification (RFID), a near field communication (NFC), a Bluetooth technology, and a Wi-Fi technology.

The extended medical test apparatus 102 typically includes at least some form of computer-readable media. Computer readable media includes any available media that can be accessed by the extended medical test apparatus 102. By way of example, computer-readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the extended medical test apparatus 102. Computer readable storage media does not include computer readable communication media.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

The computing device illustrated in FIG. 3 is also an example of programmable electronics, which may include one or more such computing devices, and when multiple computing devices are included, such computing devices can be coupled together with a suitable data communication network so as to collectively perform the various functions, methods, or operations disclosed herein.

Referring again to FIG. 3, the extended medical test apparatus 102 can include a location identification device 248. The location identification device 248 is configured to identify the location or geolocation of the extended medical test apparatus 102. The location identification device 248 can use various types of geolocating or positioning systems, such as network-based systems, handset-based systems, SIM-based systems, Wi-Fi positioning systems, and hybrid positioning systems. Network-based systems utilize service provider's network infrastructure, such as cell tower triangulation. Handset-based systems typically use the Global Positioning System (GPS). Wi-Fi positioning systems can be used when GPS is inadequate due to various causes including multipath and signal blockage indoors. Hybrid positioning systems use a combination of network-based and handset-based technologies for location determination, such as Assisted GPS.

Figure 4:
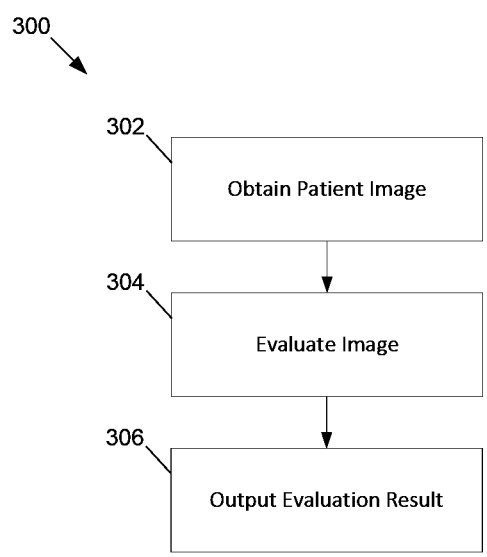
FIG. 4 is a flowchart illustrating an example method for operating the extended eye examination apparatus.

FIG. 4 is a flowchart illustrating an example method 300 for operating the extended eye examination apparatus 104. In this example, the method 300 is primarily described with respect to the extended eye exam apparatus 104 as an example of the medical test apparatus 102. It is noted that other examples of the medical test apparatus 102 can also be operated in the same or similarly manner.

Figure 7:
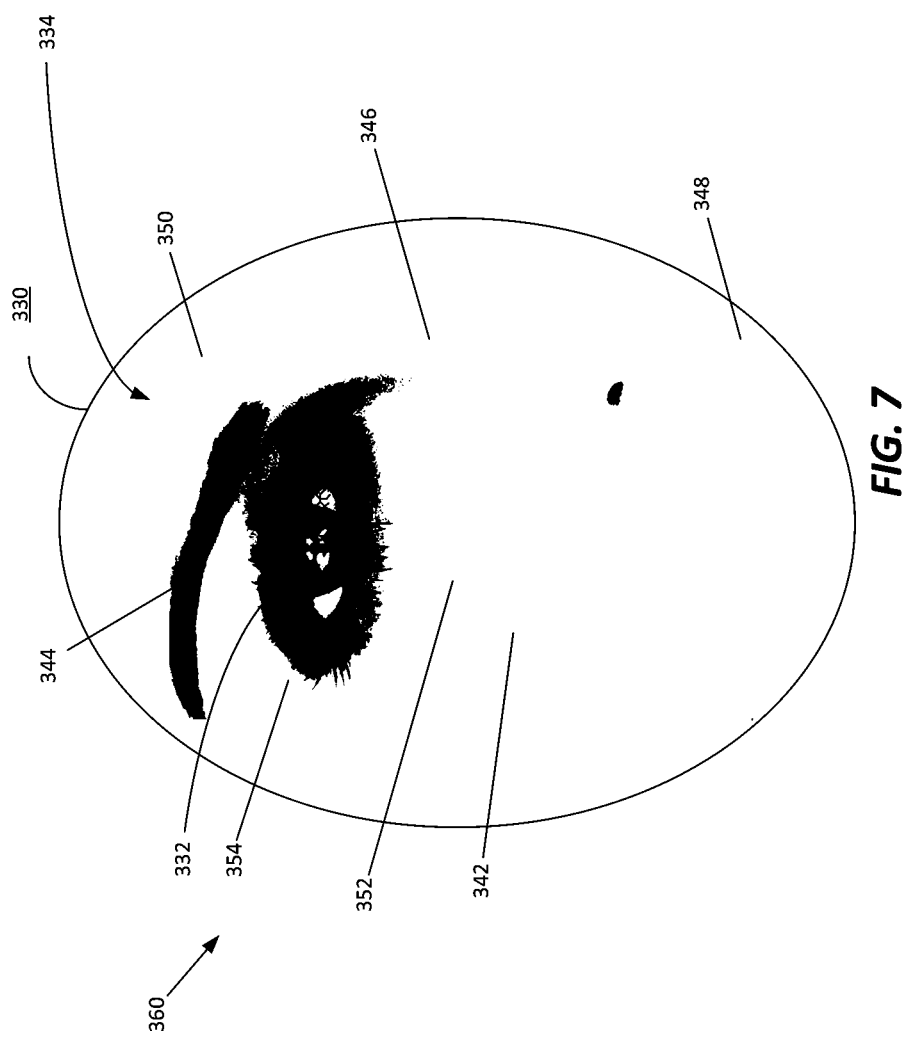
FIG. 7 illustrates an example patient image captured by the extended eye examination apparatus.

At operation 302, the eye exam apparatus 104 operates to obtain an image of a patient, such as a patient image 330 (FIG. 7). In some examples, the operation 302 can be performed by the sensing device 110 as shown in FIG. 2. In some examples, the image includes a portion of the patient body, such as a portion of the patient's face. In other examples, the image includes the whole body of the patient to detect the patient's posture or movement. In some examples, the obtained image includes the patient's eye as well as a surrounding portion of the patent around the eye. An example of the patient image is illustrated in FIG. 7.

In some examples, the eye examination apparatus 104 provides instructions to a user of the apparatus 104 so that the user can properly operate the apparatus 104 to obtain the image. Such instructions can be presented in various manners. For example, the instructions can be displayed on a screen of the apparatus 104, or verbally presented through the apparatus 104.

At operation 304, the eye exam apparatus 104 operates to evaluate the image obtained in the operation 302. In some examples, the operation 304 can be performed by the data evaluation device 112. In some examples, the eye exam apparatus 104 processes the patient image according to suitable image processing techniques, and evaluates data to generate an diagnostic result.

At operation 306, the eye exam apparatus 104 operates to output the evaluation result. The evaluation result can be presented in various manners. In some examples, the eye exam apparatus 104 includes a display device on which the evaluation result is displayed. In other examples, the evaluation result can be presented in an audible format. Other types are also possible in presenting the evaluation result.

Figure 5:
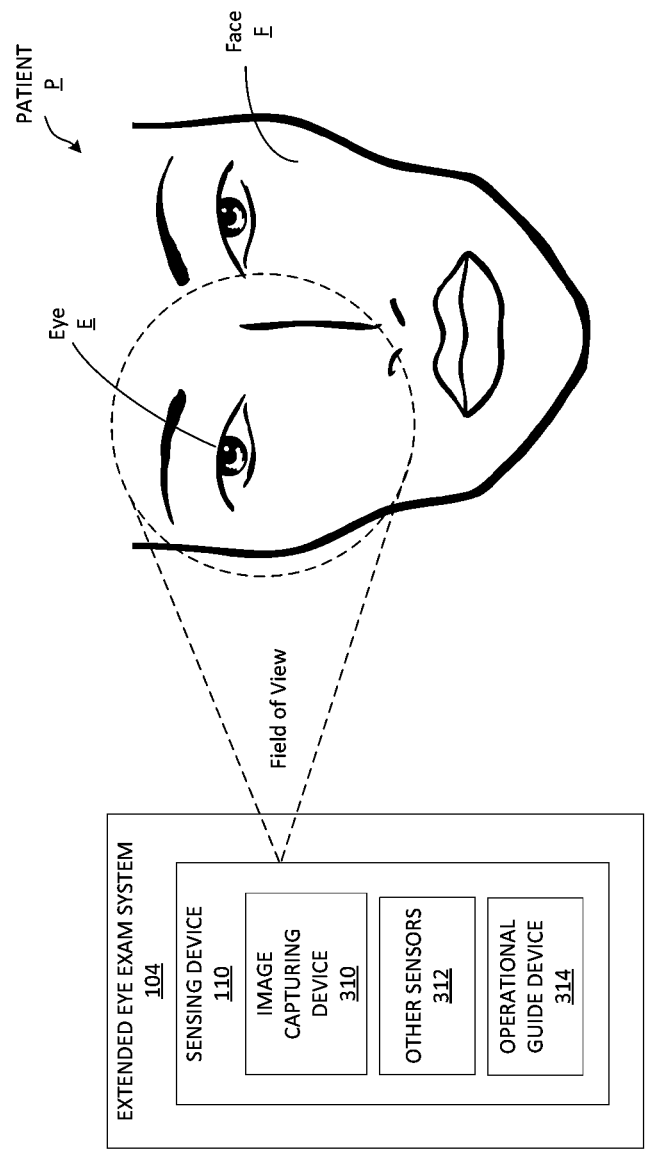
FIG. 5 illustrates an example sensing device of FIG. 2.

FIG. 5 illustrates an example of the sensing device 110 of FIG. 2. The sensing device 110 operates to obtain a patient image 330 (FIG. 7) (e.g., the operation 302 in FIG. 4). In the illustrated example, the sensing device 110 includes an image capturing device 310 and other sensors 312.

The image capturing device 310 is a device configured to capture images of the patient P, such as a portion of the patient's face F including the eye E. In some examples, the image capturing device 310 is configured to capture a visible digital image. In addition or alternatively, the image capturing device 310 can capture other types of image, such as a thermal image or infrared image. An example of the image capture device 310 is illustrated and described in more detail with reference to FIG. 6.

Alternatively or in addition, other sensors 312 can be included in the sensing device 110. Such sensors 312 are used to detect and monitor one or more physiological parameters associated with the patient, together with or separately from the patient image captured by the image capture device 310. Examples of such sensors 312 include a temperature sensor (e.g., a capacitance temperature sensor), a blood pressure sensor (e.g., an inflatable cuff operated by a pump), an infrared (IR) sensor, and other suitable sensors. For example, a temperature sensor is incorporated with a handheld medical test apparatus 102, and a user can press the temperature sensor of the apparatus 102 against a portion of the patient's body (e.g., the patent's forehead or nose) to detect the body temperature through the temperature sensor.

In general, physiological parameters can include vital signs, physiological measurements, and biological measurements, which can be detected from various portions of the patient's body. For example, physiological parameters include measurements of the body's basic functions, which are useful in detecting or monitoring medical problems. Examples of physiological parameters include body temperature, pulse rate (i.e., heart rate), respiration rate (i.e., breathing rate), blood pressure, blood gas, and SpO2. Typically, body temperature can be taken in various manners, such as orally, rectally, by ear, or by skin. The pulse rate is a measurement of the heart rate, or the number of times the heart beats per minute. The pulse rate can also indicate a heart rhythm and the strength of the pulse. The pulse can be taken on different body portions where the arteries are located, such as on the side of the neck, on the side of the elbow, or at the wrist. The respiration rate is the number of breaths a person takes per minute and is used to note whether the person has any difficulty breathing. Blood pressure is the force of the pushing against the artery walls. There may be other vital signs, such as pain, Glasgow coma scale, pulse oximetry, blood glucose level, end-tidal $CO_2$, functional status, shortness of breath, and gait speed.

In some examples, the sensing device 110 includes an operational guide device 314 configured to guide a user to properly operate the apparatus 104. For example, the operational guide device 314 operates to present instructions to a user of the apparatus 102 (e.g., the eye exam apparatus 104) so that the user can properly position the apparatus 102 relative to the patient, or properly position the patient relative to the apparatus 102, and manipulate the apparatus 102 to capture a patient image of the patient. Operational instructions can be displayed on a screen and/or verbally presented to guide the user to operate the apparatus 102.

Figure 6:
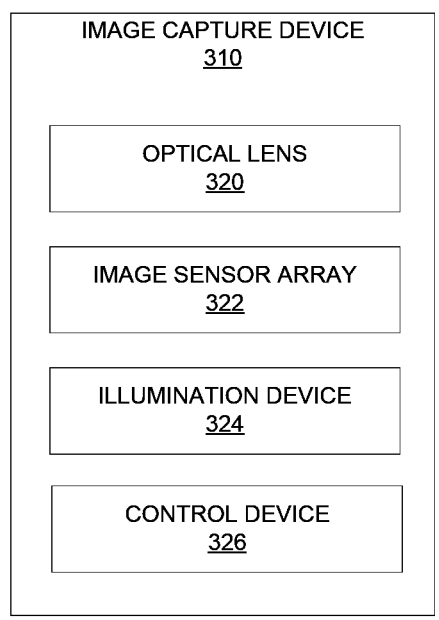
FIG. 6 illustrates an example image capture device.

FIG. 6 illustrates an example of the image capture device 310. In this example, the image capture device 310 includes an optical lens element 320, an image sensor array 322, an illumination device 324, and a control device 326.

The image capture device 310 is configured to capture images of the patient. The image capture device 310 is in communication with the data evaluation device 112. The images obtained by the image capture device 310 can be transmitted to the data evaluation device 112 for subsequent processes.

In some embodiments, the images captured by the image capture device 310 are digital images. The digital images can be captured in various formats, such as JPEG, BITMAP, TIFF, etc. In other embodiments, the images captured by the image capture device 310 are film images. In yet other embodiments, the image capture device 310 includes a digital video camera to capture videos to be used as images for evaluation purposes as described herein. Yet other embodiments of the image capture device 310 are possible as well.

In some examples, the optical lens element 320 includes a variable focal lens, such as a lens moved by a step motor, or a fluid lens (also known as a liquid lens). Other embodiments of the optical lens element 320 are also possible.

The image sensor array 322 is a device configured to receive and process light reflected by the patient. The image sensor array 322 can be of various types. For example, the image sensor array 322 is a complementary metal-oxide semiconductor (CMOS) sensor array (also known as an active pixel sensor (APS)) or a charge coupled device (CCD) sensor.

The example image sensor array 322 includes photodiodes that have a light-receiving surface and have substantially uniform length and width. During exposure, the photodiodes convert the incident light to a charge. The image sensor array 322 can be operated in various manners. In some embodiments, the image sensor array 322 is operated as a global reset, that is, substantially all of the photodiodes are exposed simultaneously and for substantially identical lengths of time. In other embodiments, the image sensor array 322 is used with a rolling shutter mechanism, in which exposures move as a wave from one side of an image to the other. Other mechanisms are also possible to operate the image sensor array 322 in yet other embodiments.

The illumination device 324 is a device configured to generate and direct light towards the patient when the image capture device 310 is in use so that the patient, such as the structures of the eye and the area surrounding the eye, may be imaged. In some embodiments, the illumination device 324 includes one or more light emitting diodes, incandescent bulbs, or fiber optic cables. Yet other embodiments of the illumination device 324 are possible as well. In some embodiments, the illumination device 324 is configured to create multiple illumination conditions, each having a different intensity (i.e., brightness) of light. However, some embodiments of the image capture device 310 do not include an illumination device 324.

The control device 326 is a device configured to control the operation of the image capture device 310 to capture images. In some embodiments, the control device 326 is configured to control the optical lens element 320, the image sensor array 322, and the illumination device 324. In some embodiments, the control device 326 is in communication with the data evaluation device 112.

FIG. 7 illustrates an example patient image 330 captured by the extended eye examination apparatus 104. In some embodiments, the patient image 330 is captured to include an eye image 332 and a facial image 334 around the eye 332. In other embodiments, other portions of the patient P can also be captured for diagnostic evaluation.

The eye image 332 is used to examine one or more structures of the eye E. Example eye structures that can be monitored include pupil, lens, iris, cornea, suspensory ligaments, ciliary body, aqueous humor, vitreous humor, sclera, choroid, retina, fovea, and other relevant elements. As described herein, such interior components of the eye can be used to discover if the patient has any eye problems or other health conditions.

In some examples, the eye exam apparatus 104 operates to illuminate and magnify the inside of the eye to capture the patient image so that the patient image is suitable to check for cataracts, retinal problems, damaged blood vessels (which can suggest diabetes or high blood pressure), and other components of the eye.

The surrounding facial image 334 includes one or more facial components which can be used to perform diagnostic evaluation of the patient's health conditions. For example, the facial components include a skin color 342, an eyebrow 344, nose 346, lip 348, forehead 350, cheek 352, surrounding eye 354, and other portions usable for evaluation as described herein.

Figure 8:
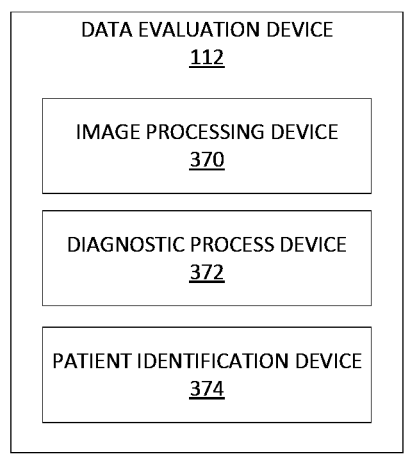
FIG. 8 is a block diagram illustrating an example data evaluation device.

FIG. 8 is a block diagram illustrating an example of the data evaluation device 112. In some examples, the data evaluation device 112 operates to process and evaluate data obtained by the sensing device 110. Where a patient image 330 is obtained by the image capturing device 310 of the sensing device 110, the data evaluation device 112 operates to process and evaluate the patient image 330. In the illustrated example, the data evaluation device 112 includes an image processing device 370, a diagnostic process device 372, and a patient identification (ID) device 374.

The image processing device 370 is a device configured to retrieve one or more patient images obtained by the image capture device 310 and process the images using various image processing techniques for further evaluation. Such image processing techniques are known in the art, including downsampling, masking, grayscaling, normalizing, blurring, and other suitable image processing methods. In some examples, the image process device 370 operates to perform image processing to determine one or more points of interest in the patient images. Such points of interest can be one or more of the facial components and/or the eye structures, which are identified in the patient image.

The diagnostic process device 372 operates to evaluate the patient image and diagnose health conditions including ophthalmologic diseases, such as cataract, uveitis, glaucoma, macular degeneration, diabetic retinopathy, etc., as well as other diseases or illnesses such as diabetes, cancer, drug overuse, brain injury, stroke, mental disorder, Alzheimer's disease, etc.

A few example diagnostic processes that can be performed by the device 372 are described below. For example, the diagnostic process device 372 can implement optical coherence tomography (OCT), which is a non-invasive imaging test that uses light waves to take cross-section pictures of the retina. Such cross-section pictures of the retina can be captured by the image capture device 310. With OCT, each of the retina's distinctive layers can be seen and examined. The thickness of each layer can help with diagnosis and provide treatment guidance for glaucoma and retinal diseases, such as age-related macular degeneration and diabetic eye disease.

In addition, the diagnostic process device 372 can detect diabetic retinopathy to detect damages to the retina due to diabetes. The diagnostic process device 372 is configured to detect changes in the blood vessels of the retina that indicate diabetic retinopathy. Diabetic retinopathy develops as prolonged exposure to high blood glucose weakens the walls of the blood vessels in the eyes. In some examples, the diagnostic process device 372 detects little red or white spots on the retina to find earlier signs of diabetic retinopathy. Such spots can be referred to as microaneurysms, which are tiny pouches of blood that have bulged through the damaged blood vessel walls and can leak blood, fat, and fluid into the retinal tissues. The diagnostic process device 372 can also detect macular edema, which is an accumulation of fluid in the macula due to leaking blood vessels that can be caused by diabetic retinopathy.

In other examples, the diagnostic process device 372 can determine a hypertension by evaluating the vasculature in the eye captured in a patient image.

The diagnostic process device 372 can diagnose high cholesterol by detecting a milky white ring (i.e., arcus senilis) around the iris. Further, the device 372 can diagnose Wilson's disease by detecting a coppery-colored ring round the eye.

The diagnostic process device 372 can evaluate blepharitis from a patient image, which can be found on the outer or inner eyelid. Further, a chalazion can be found by the diagnostic process device 372 that detects inflammation of a small cystic gland in the eyelid. The diagnostic process device 372 can evaluate a color of the eyelid, or a change in color of the eyelid, to diagnose other illnesses.

In other examples, the diagnostic process device 372 detects a motion of the eye or other facial components from patient images so as to determine various illnesses. For example, concussion screening can be performed by the diagnostic process device 372 as described herein.

In yet other examples, the diagnostic process device 372 can use images to detect a skin color at a particular point of interest, a body portion around the vasculature, the fluid in the eye, and the eye itself (e.g., ocular or caruncle images), to evaluate various medical conditions, such as diabetes, high blood sugar, temperature, and any other conditions.

For example, the device 372 can be used to monitor jaundice (also referred to as icterus) to evaluate liver function, by detecting a skin color or a change thereof. Jaundice is a yellowish pigmentation of the skin, the conjunctival membranes over the sclerae and other mucous membranes caused by high blood bilirubin levels. Jaundice is often seen in liver disease such as hepatitis or liver cancer. It may also indicate leptospirosis or obstruction of the biliary tract by, for example, gallstones or pancreatic cancer.

The patient ID device 374 operates to identify the patient, with which the medical test apparatus 102 interacts. The patient ID device 374 detects one or more biometric identifiers from a patient image captured for the patient and determines whether the biometric identifiers match corresponding characteristics of the patient.

Biometric identifiers are distinctive, measurable characteristics for labeling and describing individuals. Biometric identifiers can include physiological characteristics and behavioral characteristics. Physiological characteristics are related to the shape of the body. For example, physiological characteristics include fingerprint, palm veins, face recognition, DNA, palm print, hand geometry, iris recognition, retina and odour/scent. Behavioral characteristics are related to the pattern of behavior of a person, including typing rhythm, gait (e.g., a person's manner of moving, walking or running), and voice.

When the medical test apparatus 102 is operated to examine a patient P, the patient ID device 374 can operate to automatically identify the patient P that is being tested using the apparatus 102. In some examples, the patient ID device 374 evaluates the patient image captured by the image capture device 310 to identify the patient. For example, where the eye examination apparatus 104 is implemented, the patient ID device 374 is configured to perform a retinal scan, which uses the unique patterns on a patient's retina blood vessels, an/or iris recognition, which uses mathematical pattern-recognition techniques on video images of one or both of the irises of a patient's eyes. In other example, the patient ID device 374 performs a facial scan to identify the patient.

In other examples, the patient ID device 374 is configured to separate from the data evaluation device 112. For example, the patient ID device 374 is configured to capture other biometric data, such as fingerprint readings, thumb print readings, digit distance readings (e.g., distance between digits and lengths of digits), voice patterns, etc. Other methods can also be used in other examples.

Once the patient ID device 374 identifies a patient, the identification information can be used for a check-in service.

Figure 9:
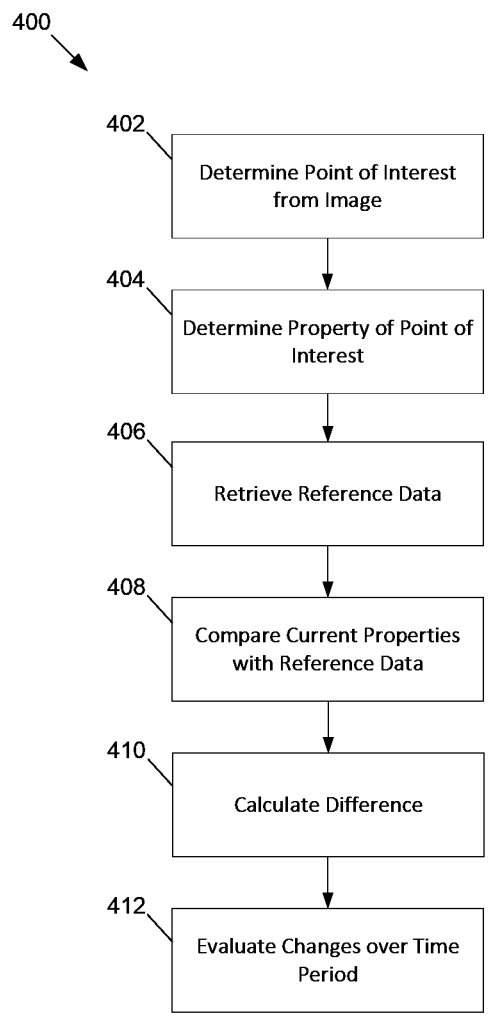
FIG. 9 is a flowchart illustrating an example method for operating the data evaluation device.

FIG. 9 is a flowchart illustrating an example method 400 for operating the data evaluation device 112. In some examples, the method 400 is at least partially performed by the diagnostic process device 372 of the data evaluation device 112.

In some examples, the method 400 can be performed locally in the medical test apparatus 102, such as the eye exam apparatus 104. In other examples, the method 400 is performed remotely from the medial test apparatus 102. For example, the method 400 can be performed a remote computing device, such as the data management system 106.

At operation 402, the data evaluation device 112 detects one or more predetermined points of interest 360 (FIG. 7) from a patient image 330. In some examples, the patient image has been processed by the image process device 370 to be suitable for evaluation in the method 400.

The points of interest are determined based on types of test performed for a patient. In the illustrated example of FIG. 7, the patient image includes one or both of a patient's eye 332 and a portion of the patient's face 334 around the eyes. In this example, examples of the points of interest include various facial components and eye structures, as illustrated in FIG. 7. For example, to diagnose hypertension, the vasculature in the eye is determined as points of interest. To screen concussion, the eye is set as a point of interest so that a motion of the eye is monitored and recorded. By way of example, the medical test apparatus 102 is configured as a handheld device which can be used to hit or tap the patient, and a motion of the patient's body or eye is monitored in response to the hitting or tapping to perform concussion screening. In other examples, such points of interest can be a skin color at a predetermined location of a patient's body or face, an eye fluid (e.g., constituents of the eye fluid), and an eye color.

At operation 404, the data evaluation device 112 determines one or more properties of the point of interest that is detected at the operation 402. By way of example, the properties of a point of interest include physical characteristics, conditions, qualities, and status of the point of interest shown in the patient image in question. Examples of such properties include physical structures, colors, motions, constituents, and any other elements that are associated with points of interest at issue. In some embodiments, the determined properties of the point of interest can be stored for subsequent or future use.

At operation 406, the data evaluation device 112 retrieves reference data. The reference data is used as a reference point for evaluating the properties of the point of interest obtained at the operation 404. In some examples, the reference date includes properties of the same point of interest obtained from another patient image. Such another patient image can be a patient image which was captured at a previous time (e.g., the last time).

At operation 408, the data evaluation device 112 operates to compare the properties of the point of interest from the current patient image with the reference data. The reference date includes properties of the same point of interest at a previous time.

At operation 410, the data evaluation device 112 calculates a difference between the current properties and the previous properties.

Figure 10:
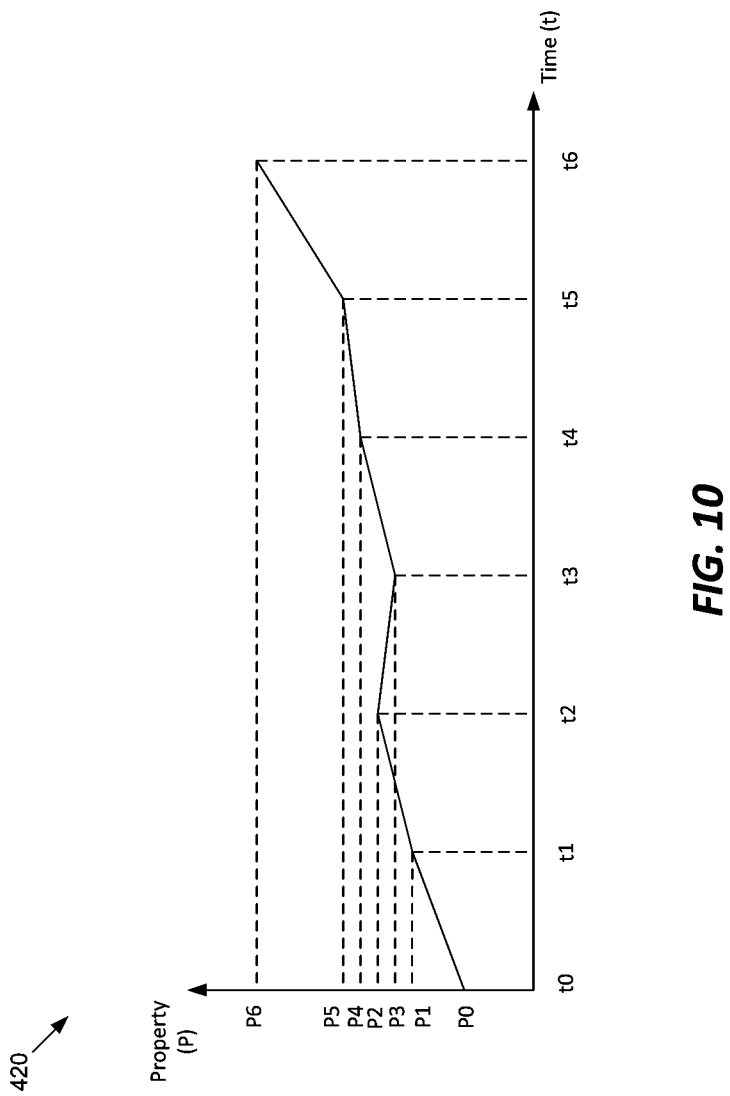
FIG. 10 graphically illustrates an example trend that is evaluated in the method in FIG. 9.

At operation 412, the data evaluation device 112 evaluates a change in the properties over a period of time. In some examples, the period of time corresponds to a time between when the current patient image was captured and when the previous patient image was captured. Such a change in the properties can be used to show a trend of the properties of the point of interest, as illustrated in FIG. 10. As described herein, the data evaluation device 112 can provide automated evaluation or diagnosis based on the trend of the properties.

FIG. 10 graphically illustrates an example trend 420 that is evaluated in the method 400 in FIG. 9. In the illustrated graph, a time (t) indicates a time when a patient is tested with the medical test apparatus 102, and a property (P) indicates a property at a point of interest, the property being determined from a patient image captured at a time of, or shortly before, such determination.

The data evaluation device 112 can store the values (e.g., P0-P6) of a property associated with a particular point of interest at different times (e.g., t0-t6). By way of example, where the data evaluation device 112 evaluates a patient image taken at, or shortly before, a time (t6), the data evaluation device 112 obtains a value (P6) of a property at a predetermined point of interest. As described above, the data evaluation device 112 then operates to compare the property value (P6) with reference data. Such reference data includes a value of the property at the point of interest that has been obtained at a time prior to the time (t6). In some examples, the reference data is a property value (P5) associated with the last time (t5) when a patient image was taken and the same point of interest was evaluated by the data evaluation device 112. In other examples, the reference data is any property value (P0-P5) that was obtained at any previous time (t0-t5).

With a plurality of property values at different times, the data evaluation device 112 can determine a trend 420 of the property at the point of interest. For example, where a point of interest is set as a patient's forehead, a property to be monitored can be determined as a color, and the data evaluation device 112 detects the colors at the forehead from patient images obtained at different times and evaluates a change in color at the forehead shown in the patient images. Such a trend can be used to diagnose one or more illnesses or medical conditions.

In some examples, the trend data is stored in the medical test apparatus 102. In other examples, the trend date is stored in a remote computing device, such as the data management system 106, and is retrievable by the medical test apparatus 102 for use in evaluation.

In some examples, the trend data can also be used to determine any erroneous measurement and/or evaluation from the medical test apparatus 102. For example, if one or more measurements are significantly deviated from the other measurements that generally follow a trend, such one or more measurements can be evaluated to determine whether they were erroneously obtained. Other methods are also possible in other examples.

FIG. 11 schematically illustrates an example evaluation output 430 presented by the output device 114 of the medical test apparatus 102. The evaluation output 430 includes various pieces of information associated with the patient and the test result. In the illustrated example, the evaluation output 430 includes patient information 432, measurement data 434, and diagnostic result information 436.

The evaluation output 430 can be presented in various manners. In the illustrated example, the evaluation output 430 is displayed on a display screen of the medical test apparatus 102. In other examples, the evaluation output 430 is displayed on a display screen of a remote computing device. In yet other examples, the evaluation output 430 is printed out as a report using a printing device.

The patient information 432 can include patient's biographical information, physiological information, and/or other medical data. In some examples, at least some of the patient information 432 can be transmitted from the data management system 106.

The measurement data 434 shows the trend of the properties of a point of interest in various formats. For example, the data regarding the change in the properties over time can be presented in a table, and/or plotted to a graphical presentation.

The diagnostic result information 436 includes a diagnosis derived from the measurement data. In addition, the diagnostic result information 436 can include a recommendation generated based on the diagnosis. For example, the diagnostic result information 436 includes a feedback of the test, such as a current status, a past status, and a trend over time, and any suggestions for improvement, such as diet and exercise recommendations. Further, the diagnostic result information can include a measure of progression of the illnesses or disorders, the efficiency of undergoing treatment, and a referral to another healthcare practitioner.

Although the evaluation output 430 is primarily illustrated as being configured to deliver various pieces of information together, it is also possible to design the evaluation output 430 as a simple notification, such as a notification for alarming a predetermined condition or status. For example, when it is determined that a property of a point of interest found in a patient image meets a predetermined condition, an alarm or notification is generated and provided in the medical test apparatus 102.

As such, the medical test apparatus of the present disclosure provides diagnosis, health advice, and/or wellness advice using a single apparatus at a single location with a single visit to a healthcare practitioner, such as a primary physician. The apparatus can generate various medical and/or healthcare services, such as providing advice and/or recommendations about a medical condition, diagnosing and/or treating a medical condition, providing referral services for a medical condition, prescribing medicine for a medical condition, monitoring a medical condition, providing follow-up checks for a medical condition, providing routine check-up services, providing advice, counseling, and/or recommendations about medical and/or health matters, providing a course of treatment for a medical condition, providing health counseling, providing health information, and providing wellness counseling and information. As can be appreciated, additional services can be provided to patents.

Although it is described that the eye exam apparatus 104 performs the image processing and evaluation, it is also possible in other embodiments that the data management system 106 instead performs the image processing and evaluation. In such embodiments, the eye exam apparatus 104 transmits data associated with the patient image to the data management system 106, and the data management system 106 operates to process and evaluate the data in the same or similar manner as described above. The data management system 106 can generate an evaluation result, which is then transmitted to the eye exam apparatus 104 or other computing devices so that the eye exam apparatus 104 or other computing devices present the result.

Referring to FIGS. 12-15, example structures of the extended medical test apparatus 102 are illustrated.

Figure 12:
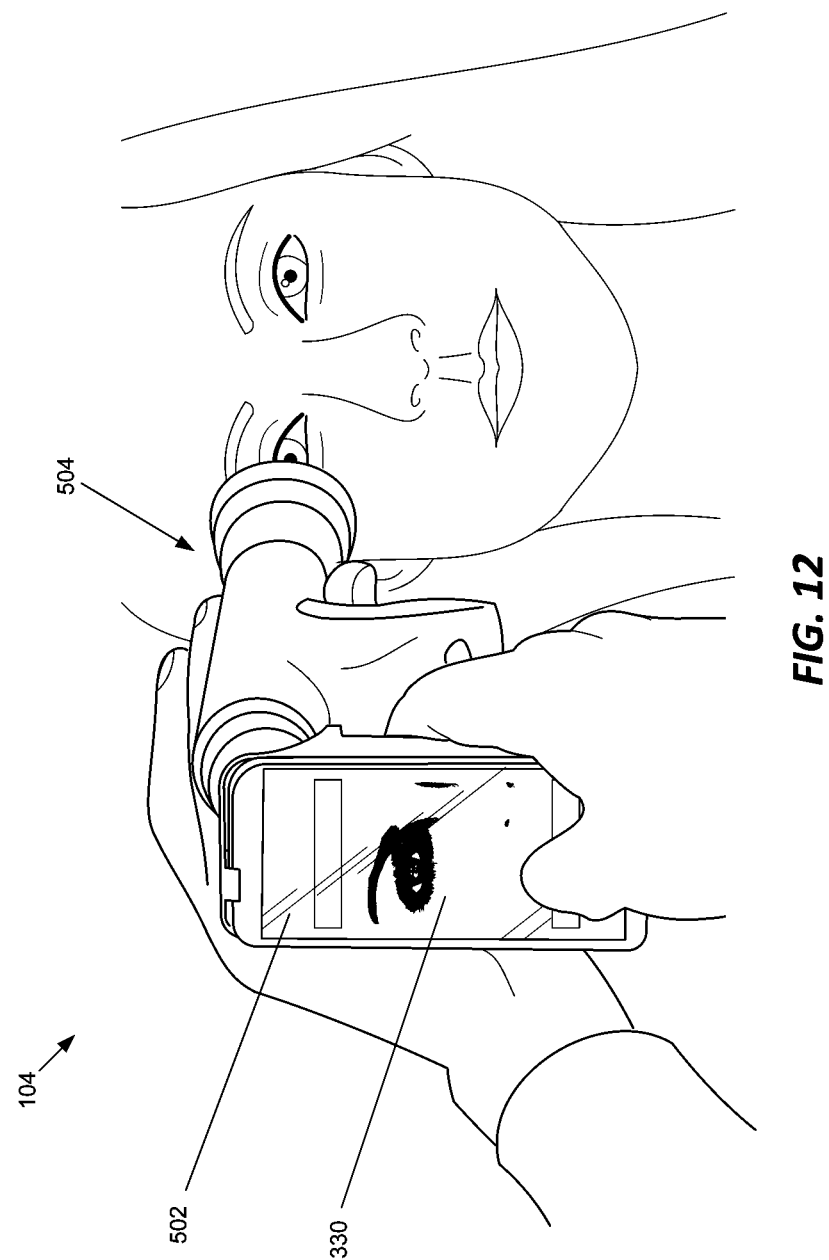
FIG. 12 schematically illustrates an example of the extended eye examination apparatus.

FIG. 12 schematically illustrates an example of the extended eye examination apparatus 104. In this example, the extended eye exam apparatus 104 includes a mobile computing device 502 and an attachment device 504 configured to be connected to the mobile computing device 502.

As illustrated, a user, such as a primary care practitioner, can easily attach the attachment device 504 to an existing mobile computing device 502. The user can take an image of the patient while monitoring a screen of the mobile computing device 502. This helps the user to position the apparatus 104 properly to capture a desired patient image 330. As illustrated, the apparatus 104 can image the eye and a portion of the face around the eye.

In some examples, the attachment device 504 is configured to be conveniently held by a user (e.g., a healthcare practitioner or a patient) so that the user support the device 504 at a predetermined position close to the patient and capture a patient image 330 as desired. For example, the apparatus 102 (e.g., the attachment device 504) can be used with PanOptic™ Ophthalmoscope or iExaminer™ from Welch Allyn of Skaneateles Falls, N.Y. Other examples of the apparatus 102 can employ at least part of the disclosure in U.S. patent application Ser. No. 14/633,601, titled THROUGH FOCUS RETINAL IMAGE CAPTURING, filed Feb. 27, 2015, the disclosure of which is incorporated herein by reference in its entirety. Another example fundus image capture apparatus 102 is configured similarly to a device disclosed in U.S. patent application Ser. No. 14/557,146, titled DIGITAL COLPOSCOPE SYSTEM, filed Dec. 1, 2014, the entirety of which is incorporated herein by reference.

In other embodiments, the physical structure of the apparatus 102 includes a support structure configured to couple to a patient. For example, the support structure is an eye glasses frame or a headband. An example of the physical structure of this type is disclosed in U.S. patent application Ser. No. 14/177,594, titled OPHTHALMOSCOPE DEVICE, filed Feb. 11, 2014, the disclosure of which is incorporated herein by reference in its entirety.

Figure 13:
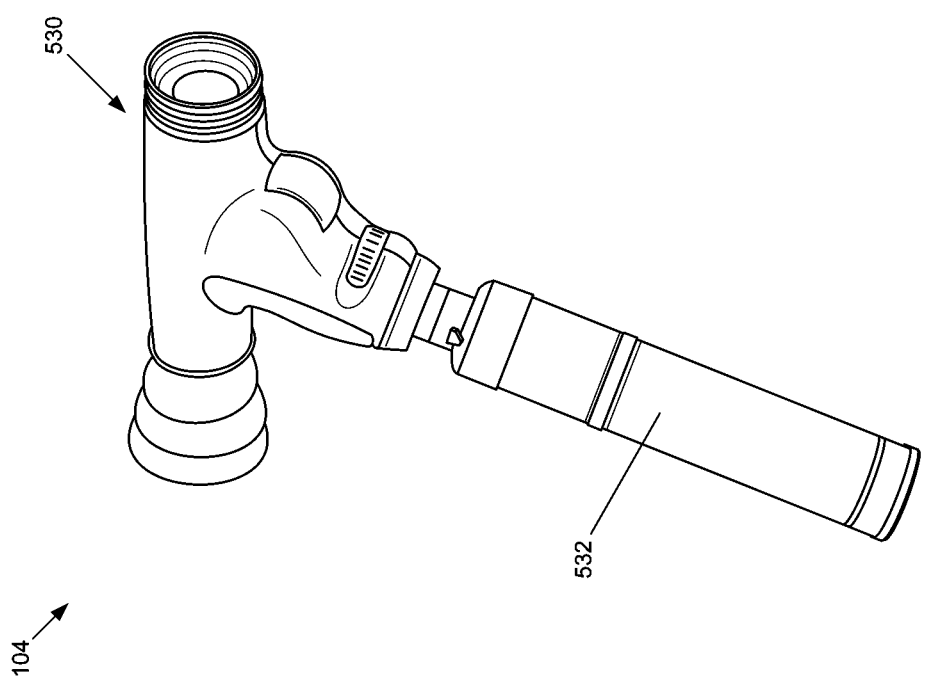
FIG. 13 schematically illustrates another example of the extended medical test apparatus.

FIG. 13 schematically illustrates another example of the extended medical test apparatus 102. In this example, the apparatus 102 is configured as an independent handheld device 530. Similarly to the example of FIG. 12, the apparatus 102 in this example has a physical structure configured to be held by the user for viewing and capturing patient images. For example, the apparatus 102 can be used with PanOptic™ Ophthalmoscope from Welch Allyn of Skaneateles Falls, N.Y.

Figure 14:
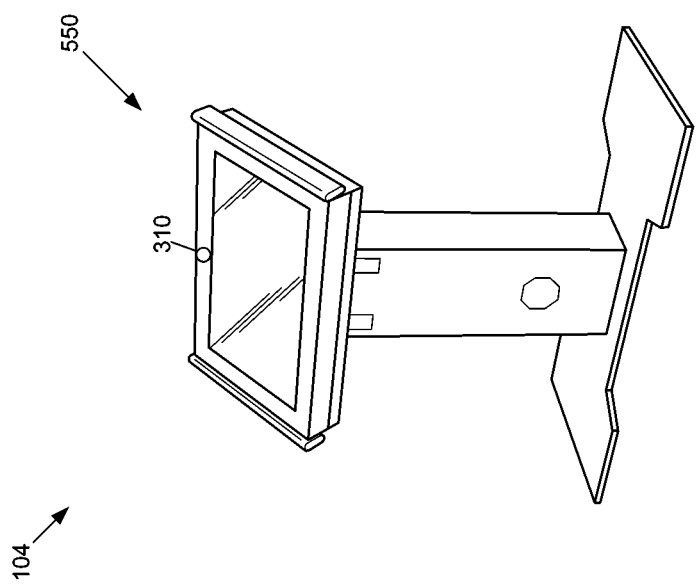
FIG. 14 schematically illustrates yet another example of the extended medical test apparatus.

FIG. 14 schematically illustrates yet another example of the extended medical test apparatus 102. In this example, the apparatus 102 is configured as a standalone station 550, such as a kiosk.

In some examples, the apparatus 102 is installed in controlled environment, such as a doorway to a clinic or a doctor's room, and other areas where people can walk by. A patient can come close and stand in front of the standalone station 550 so that the apparatus 102 captures a patient image from the patient.

In some examples, the apparatus 102 provides instructions to a user (e.g., a patient) of the apparatus 102 so that the user is properly positioned to be tested by the apparatus 102. By way of example, instructions are displayed on a screen and/or verbally presented to guide a user to position him or herself appropriately for image capturing. For example, the user can be prompted to look into a particular location of the apparatus 102 such that the image capture device 310 captures a desirable image (e.g., a patient image as described herein), and/or other sensors detects parameters associated with the user.

In some examples, the apparatus 102 is configured to perform a macro scan. For example, the apparatus 102 can capture a patient image for a large portion of the patient or the entire body of the patient. The apparatus 102 can operate to instruct the patient to pose differently so as to capture a plurality of patient images for different portions of the patient, different views of the patient, and/or different types of posture of the patient. The apparatus 102 can further detect one or more characteristics of a patient's gait, such as a manner and/or speed of moving, walking or running. For example, the apparatus 102 can evaluate the patient's improvement (e.g., a patient's post-surgical improvement such as a hip replacement surgery, or the effectiveness of physical therapy) by monitoring a change in the patient's gait over time.

In other examples, the apparatus 102 is configured to perform a micro scan. For example, the apparatus 102 captures a patient image for a limited area of the patient, such as a facial scan, a head, a particular spot in the face, and other areas on the patient's body.

Figure 15:
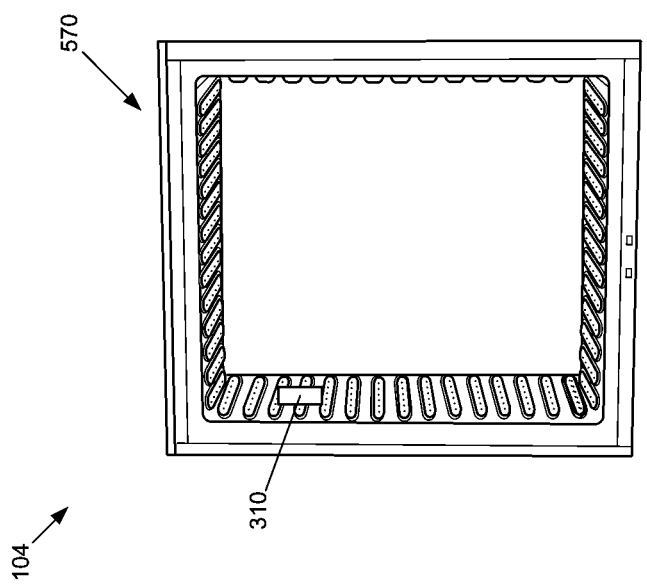
FIG. 15 schematically illustrates yet another example of the extended medical test apparatus.

FIG. 15 schematically illustrates yet another example of the extended medical test apparatus 102. In this example, the apparatus 102 is configured as a walk-through frame 570. The apparatus 102 can be installed in various locations through which patients can pass. For example, the apparatus 102 is installed at a gate or entrance of a clinic or a door to a physician. In other examples, the apparatus 102 can also be placed in a separate examination room. The functions and operations of the walk-through frame 570 are similar to the standalone station 550 in FIG. 14.

As such, the medical test apparatus of the present disclosure provides user-friendly medical instruments that are configured to perform a variety of measurements at the same time and provide accurate reliable diagnosis, so that a patient or anyone, such as a primary care provider, who has less skills and experience in particular medical fields can use the instruments with the same comfort level as well-trained healthcare practitioners.

The various examples and teachings described above are provided by way of illustration only and should not be construed to limit the scope of the present disclosure. Those skilled in the art will readily recognize various modifications and changes that may be made without following the example examples and applications illustrated and described herein, and without departing from the true spirit and scope of the present disclosure.

What is claimed is:

1. An apparatus for a medical test, the apparatus comprising:
   an image capture device configured to capture a patient image, the patient image including an eye and a surrounding facial portion around the eye; and
   an evaluation device configured to:
      determine a point of interest associated with the surrounding facial portion in the patient image, the point of interest determined based on a type of the medical test, wherein the point of interest includes:
      (i) a first point of interest being selected from the eye in the patient image for imaging a portion of the eye associated with the first point;
      and (ii) a second point of interest being selected from the surrounding facial portion around the eye in the patient image;
      determine a property associated with the surrounding facial portion of the second point of interest from the patient image;
      compare the property with a reference property associated with the surrounding facial portion; and
      evaluate a change in the property associated with the surrounding facial portion based on a difference between the property and the reference property over a period of time to provide a medical diagnosis.

2. The apparatus of claim 1, wherein the evaluation device is further configured to generate a diagnosis based on the change in the property.

3. The apparatus of claim 2, wherein the evaluation device is further configured to generate a recommendation based on the diagnosis.

4. The apparatus of claim 1, further comprising an output device configured to present an evaluation output, the evaluation output including the change in the property.

5. The apparatus of claim 4, wherein the output device includes a display screen configured to display the evaluation output.

6. The apparatus of claim 1, wherein the image capture device captures the patient image at a first time and captures a reference image at a second time prior to the first time, and the evaluation device is further configured to:
   determine the point of interest in the reference image;
   determine the reference property associated with the point of interest from the reference image; and
   evaluate the change in the property, the period of time being determined by a difference between the first time and the second time.

7. The apparatus of claim 1, wherein the first point of interest is selected from a group consisting of pupil, lens, iris, cornea, suspensory ligaments, ciliary body, aqueous humour, vitreous humor, sclera, choroid, retina, and fovea of the eye.

8. The apparatus of claim 1, wherein the second point of interest is selected from a group consisting of a skin color, an eyebrow, a nose, a lip, a forehead, a cheek, and a surrounding eye.

9. The apparatus of claim 1, further comprising a patient identification device configured to evaluate the patient image and identify a patient associated with the patient image.

10. The apparatus of claim 1, further comprising a handheld structure configured to house the image capture device and the evaluation device.

11. The apparatus of claim 1, further comprising an attachment device configured to attach a mobile computing device, wherein a combination of the attachment device and the mobile computing device includes the image capture device and the evaluation device.

12. The apparatus of claim 1, further comprising a stand-alone station configured to include the image capture device and the evaluation device.

13. The apparatus of claim 1, further comprising a walk-through frame configured to include the image capture device and the evaluation device.

14. A method of performing a medical test, the method comprising:
   obtaining a patient image, the patient image including an eye and a surrounding facial portion around the eye;
   determining a point of interest associated with the surrounding facial portion in the patient image, the point of interest determined based on a type of the medical test, wherein determining the point of interest includes:
      determining a first point of interest selected from the eye in the patient image for imaging a portion of the eye associated with the first point; and
      determining a second point of interest selected from the surrounding facial portion in the patient image;
   determining a property associated with the surrounding facial portion of the second point of interest from the patient image;
   comparing the property with a reference property associated with the surrounding facial portion; and
   evaluating a change in the property associated with the surrounding facial portion based on a difference between the property and the reference property over a period of time to provide a medical diagnosis.

15. The method of claim 14, wherein the patient image is obtained at a first time, and the method further comprises:
   obtaining a reference image at a second time prior to the first time, the reference image including the eye and the surrounding facial portion;
   determining the point of interest in the reference image;
   determining the reference property associated with the point of interest from the reference image;
   evaluating the change in the property, the period of time being determined by a difference between the first time and the second time.

16. The method of claim 14, further comprising:
   presenting an evaluation output via an output device, the evaluation output including the change in the property.

17. The method of claim 14, wherein the first point of interest is selected from a group consisting of pupil, lens, iris, cornea, suspensory ligaments, ciliary body, aqueous humour, vitreous humor, sclera, choroid, retina, and fovea of the eye; and
   wherein the second point of interest is selected from a group consisting of a skin color, an eyebrow, a nose, a lip, a forehead, a cheek, and a surrounding eye.

18. The method of claim 14, further comprising:
   identifying a patient based on the patient image.

* * * * *